US00PP25689P2

(12) United States Plant Patent
Jackson et al.

(10) Patent No.: US PP25,689 P2
(45) Date of Patent: Jul. 14, 2015

(54) PERSIMMON TREE NAMED 'JN5'

(50) Latin Name: *Diospyros virginiana*
Varietal Denomination: JN5

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

( * ) Notice: Subject to any disclaimer, the term of this patent is extended or adjusted under 35 U.S.C. 154(b) by 85 days.

(21) Appl. No.: 13/987,780

(22) Filed: Aug. 31, 2013

(51) Int. Cl.
*A01H 5/08* (2006.01)

(52) U.S. Cl.
USPC ..... Plt./156

(58) Field of Classification Search
USPC ..... Plt./156
CPC ..... A01H 5/08; A01H 5/00
See application file for complete search history.

*Primary Examiner* — Kent L Bell
(74) *Attorney, Agent, or Firm* — C. A. Whealy

(57) ABSTRACT

A new and distinct cultivar of Persimmon tree named 'JN5', characterized by its upright columnar and weeping plant habit; vigorous growth habit and rapid growth rate; relatively large leaves; light orange-colored mature fruits; and good garden performance.

2 Drawing Sheets

Botanical designation: *Diospyros virginiana.*
Cultivar denomination: 'JN5'.

BACKGROUND OF THE INVENTION

The present invention relates to a new and distinct Persimmon plant, botanically known as *Diospyros virginiana* and hereinafter referred to by the name 'JN5'.

The new Persimmon plant originated from an open-pollination in Belvidere, Tenn. of an unidentified selection of *Diospyros virginiana,* not patented, as the female, or seed, parent with an unknown selection of *Diospyros virginiana* as the male, or pollen, parent. The new Persimmon plant was discovered and selected by the Inventors as a single plant within the progeny of the stated open-pollination in a controlled nursery environment in Belvidere, Tenn. during the spring of 2007.

Asexual reproduction of the new Persimmon plant by bud grafting onto a seedling Persimmon rootstock in a controlled environment in Belvidere, Tenn. since the summer of 2008 has shown that the unique features of this new Persimmon plant are stable and reproduced true to type in successive generations.

SUMMARY OF THE INVENTION

Plants of the new Persimmon have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'JN5'. These characteristics in combination distinguish 'JN5' as a new and distinct Persimmon plant:

1. Upright columnar and weeping plant habit.
2. Vigorous growth habit and rapid growth rate.
3. Relatively large leaves.
4. Fruits that become light orange in color with development.
5. Good garden performance.

Plants of the new Persimmon can be compared to plants of the female parent selection. Plants of the new Persimmon differ primarily from plants of the female parent selection in the following characteristics:

1. Plants of the new Persimmon and the female parent selection differ in plant habit as plants of the female parent selection are outwardly spreading with pendulous lateral branches.
2. Plants of the new Persimmon are more vigorous and faster growing than plants of the female parent selection.
3. Leaves of plants of the new Persimmon are larger than leaves of plants of the female parent selection.

Plants of the new Persimmon can also be compared to plants of *Diospyros khaki* 'Nuevo Rojo Brillante', disclosed in U.S. Plant Pat. No. 20,729, and *Diospyros khaki* 'Doc's Delight', disclosed in U.S. Plant Pat. No. 16,822. In side-by-side comparisons, plants of the new Persimmon differed primarily from plants of 'Nuevo Rojo Brillante' and 'Doc's Delight' in the following characteristics:

1. Plants of the new Persimmon and 'Nuevo Rojo Brillante' and 'Doc's Delight' differed in plant habit as plants of 'Nuevo Rojo Brillante' and 'Doc's Delight' were upright and not weeping.
2. Fruits of plants of the new Persimmon were smaller than fruits of plants of 'Nuevo Rojo Brillante' and 'Doc's Delight'.

BRIEF DESCRIPTION OF THE PHOTOGRAPHS

The accompanying colored photographs illustrate the overall appearance of the new Persimmon plant showing the colors as true as it is reasonably possible to obtain in colored reproductions of this type. Colors in the photographs may differ slightly from the color values cited in the detailed botanical description which accurately describe the colors of the new Persimmon plant.

The photograph on the first sheet is a side perspective view of a typical tree of 'JN5'.

The photograph on the second sheet is a close-up view of a typical tree of 'JN5' with immature fruits.

DETAILED BOTANICAL DESCRIPTION

The aforementioned photographs and following observations, measurements and values describe trees grown during the summer in 15-gallon containers in an outdoor nursery in Park Hill, Okla. and under cultural practices typical of commercial Persimmon production. During the production of the plants, day temperatures averaged 22° C. and night temperatures averaged 9° C. Plants were four years old when the photographs and description were taken. In the description, color references are made to The Royal Horticultural Society Colour Chart, 2001 Edition, except where general terms of ordinary dictionary significance are used.

Botanical classification: *Diospyros virginiana* 'JN5'.

Parentage:

*Female, or seed, parent*.—Unidentified selection of *Diospyros virginiana*, not patented.

*Male, or pollen, parent*.—Unknown selection of *Diospyros virginiana*, not patented.

Propagation:

*Type*.—Bud-grafted onto a seedling Persimmon rootstock.

*Root description*.—Thick, coarse and fleshy; dark brown, close to 200B in color.

*Rooting habit*.—Moderately freely branching; medium density.

Plant description:

*Plant and growth habit*.—Deciduous tree; upright columnar and weeping plant habit; vigorous growth habit and rapid growth rate; freely branching habit.

*Plant height*.—About 6.1 meters.

*Plant diameter* (*area of spread*).—About 2.4 meters.

Lateral branch description:

*Length*.—Variable depending on position on the tree.

*Diameter*.—Variable depending on position on the tree.

*Internode length*.—About 10 cm to 12 cm.

*Aspect*.—Pendulous.

*Strength*.—Strong.

*Texture*.—Pubescent when developing and becoming smooth and glabrous with maturity.

*Color*.—Close to 200D.

Leaf description:

*Arrangement*.—Alternate, single; relatively large.

*Length*.—About 13.3 cm.

*Width*.—About 6.1 cm.

*Shape*.—Ovate to elliptical.

*Apex*.—Acute.

*Base*.—Rounded.

*Margin*.—Entire.

*Texture, upper and lower surfaces*.—Pubescent.

*Venation pattern*.—Pinnate.

*Color*.—Developing leaves, upper surface: Close to 137A. Developing leaves, lower surface: Close to 138B. Fully expanded leaves, upper surface: Close to 139A and 137A; venation, close to 160B; fall color, close to 71A. Fully expanded leaves, lower surface: Close to 138B; venation, close to 160B.

*Petioles*.—Length: About 2.24 cm. Diameter: About 3.2 mm. Texture, upper and lower surfaces: Pubescent. Color, upper surface: Close to 147B. Color, lower surface: Close to 147C.

Flower description:

*Flower arrangement and flowering habit*.—Dioecious; pistillate flowers solitary; staminate flowers in clusters with about three flowers per cluster; freely flowering habit; flowers roughly urn to bell-shaped; flowers mostly drooping.

*Natural flowering season*.—Plants of the new Persimmon flower in May to June in Oklahoma.

*Flower longevity*.—Flowers last about two to three weeks on the plant; flowers persistent.

*Fragrance*.—Moderately fragrant.

*Flower diameter, pistillate and staminate flowers*.—About 7 mm.

*Flower length, pistillate flowers*.—About 1.54 cm.

*Flower length, staminate flowers*.—About 8.5 mm.

*Flower depth, pistillate and staminate flowers*.—About 1.1 cm to 1.5 cm.

*Flower buds, pistillate and staminate flowers*.—Length: About 6.35 mm. Diameter: About 3.8 mm. Shape: Conical; winged. Color: Close to 82A to 82B; towards the base, close to N77A.

*Petals, pistillate and staminate flowers*.—Arrangement: Typically four petals in a single whorl; petals imbricate. Length: About 7 mm to 11 mm. Width: About 6 mm to 8 mm. Shape: Broadly ovate. Apex: Mucronate, reflexed. Base: Obtuse. Margin: Entire. Texture, upper and lower surfaces: Smooth, glabrous. Color: When opening and fully opened, upper surface: Close to 155B. When opening and fully opened, lower surface: Close to 155C.

*Sepals, pistillate and staminate flowers*.—Arrangement: Typically four sepals in a single whorl. Length: About 2 mm. Width: About 1.8 mm. Shape: Broadly ovate. Apex: Truncate. Base: Acute. Margin: Entire. Texture, upper and lower surfaces: Smooth, glabrous. Color, upper surface: Close to 191C. Color, lower surface: Close to 191D.

*Peduncles, pistillate flowers*.—Length: About 6 mm to 8 mm. Diameter: About 2 mm. Strength: Strong. Texture: Smooth, glabrous. Color: Close to 191C.

*Peduncles, staminate flowers*.—Length: About 1 cm to 1.2 cm. Diameter: About 3 mm. Strength: Strong. Texture: Smooth, glabrous. Color: Close to 191C.

*Pedicels, staminate flowers only*.—Length: About 4 mm. Diameter: About 3 mm. Strength: Strong. Texture: Smooth, glabrous. Color: Close to 191C.

*Reproductive organs*.—Androecium: Stamen number: About 16 per flower. Filament length: About 2 mm to 4 mm. Filament texture: Slightly pubescent. Filament color: Close to 196C. Anther shape: Round to slightly oblong. Anther length: Less than 1 mm. Anther color: Close to 195D. Amount of pollen: Abundant. Pollen color: Close to 161A. Gynoecium: Pistil number: One per flower. Pistil length: About 1 cm. Style length: About 1 mm. Style color: Close to 71C. Stigma shape: Elliptical. Stigma color: Close to 145C. Ovary color: Close to 137B.

*Seeds and fruits, pistillate flowers only*.—Seed length: About 2 cm. Seed diameter: About 1.3 cm. Seed color: Close to 202A. Fruit length: About 2.6 cm to 3.9 cm. Fruit diameter: About 2.54 cm to 3.81 cm. Fruit shape: Globose. Fruit texture: Smooth. Fruit color, developing: Close to 195C. Fruit color, fully developed: Close to 24B.

Garden performance: Plants of the new Persimmon have been observed to have good garden performance and to tolerate wind, rain and temperatures ranging from about −29° C. to about 43° C.

Pathogen & pest resistance: Plants of the new Persimmon have not been observed to be resistant to pathogens and pests common to Persimmon plants.

It is claimed:

1. A new and distinct Persimmon tree named 'JN5' as illustrated and described.

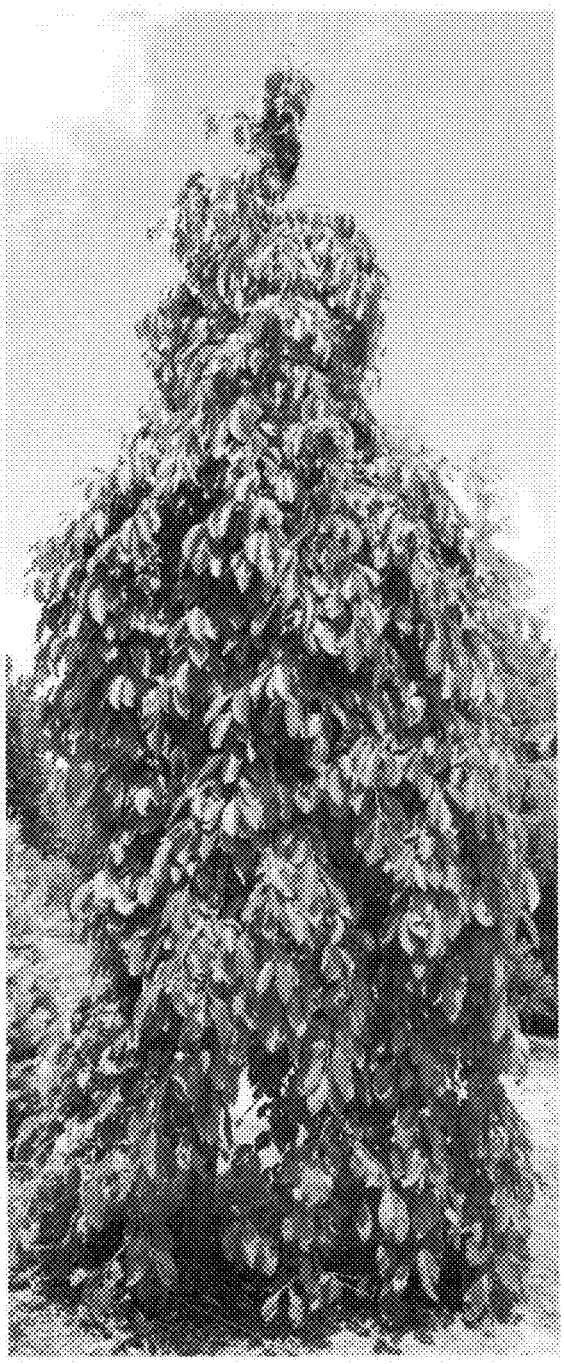

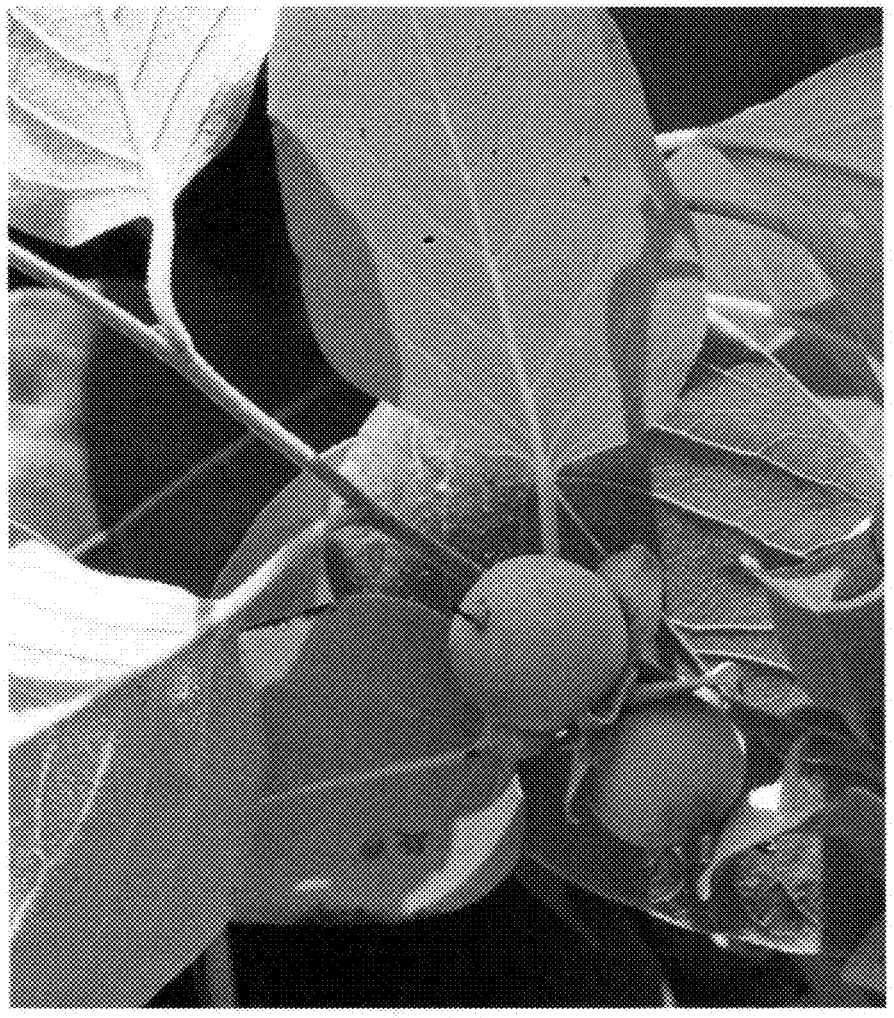

* * * * *